United States Patent [19]
Williams et al.

[11] Patent Number: 5,114,425
[45] Date of Patent: May 19, 1992

[54] METHOD AND APPARATUS FOR DETECTING ACTUAL OR LIKELY ADULTERATION OF CRITICAL USE GLOVES

[75] Inventors: Robert E. Williams; William H. Marshall; Robert B. Stout; John J. McCourt, Jr., all of Houston, Tex.

[73] Assignee: Novatec Medical Products, Inc., Houston, Tex.

[21] Appl. No.: 528,926

[22] Filed: May 25, 1990

[51] Int. Cl.$^5$ .............................................. A61B 17/36
[52] U.S. Cl. ..................................... 606/034; 340/540
[58] Field of Search ..................... 606/32, 34; 340/540

[56] References Cited

U.S. PATENT DOCUMENTS

| | | |
|---|---|---|
| 2,297,837 | 10/1942 | Loughnane . |
| 2,622,129 | 12/1952 | Killian . |
| 2,981,886 | 4/1961 | Beck . |
| 3,093,793 | 6/1963 | Hicken . |
| 3,414,808 | 12/1968 | Thomas . |
| 3,544,841 | 12/1970 | Peel . |
| 3,858,114 | 12/1974 | Voellmin et al. . |
| 3,980,073 | 9/1976 | Shaw, IV . |
| 3,980,077 | 9/1976 | Shaw, IV . |
| 4,094,320 | 6/1978 | Newton et al. . |
| 4,122,854 | 10/1978 | Blackett . |
| 4,173,229 | 11/1979 | Halfon . |
| 4,184,486 | 1/1980 | Papa . |
| 4,200,104 | 4/1980 | Harris . |
| 4,200,105 | 4/1980 | Gonser . |
| 4,231,372 | 11/1980 | Newton . |
| 4,243,932 | 1/1981 | Kakumoto . |
| 4,244,371 | 1/1981 | Farin . |
| 4,245,649 | 1/1981 | Schmidt-Anderson . |
| 4,273,531 | 6/1981 | Hasegawa . |
| 4,303,073 | 12/1981 | Archibald . |
| 4,321,925 | 3/1982 | Hoborn . |
| 4,343,308 | 8/1982 | Gross . |
| 4,365,637 | 12/1982 | Johnson . |
| 4,459,993 | 7/1984 | Foreman . |
| 4,494,541 | 1/1985 | Archibald . |
| 4,525,814 | 6/1985 | Woodall . |
| 4,575,476 | 3/1986 | Podell et al. . |
| 4,583,039 | 4/1986 | Kolcio . |
| 4,687,004 | 8/1987 | Zenkich . |
| 4,736,157 | 4/1988 | Betker . |
| 4,740,757 | 4/1988 | Converse . |
| 4,751,467 | 6/1988 | Cooper . |
| 4,754,757 | 7/1988 | Feucht . |
| 4,788,977 | 12/1988 | Farin . |
| 4,810,971 | 3/1989 | Marable . |
| 4,841,966 | 6/1989 | Hagen . |
| 4,843,014 | 6/1989 | Cukier . |
| 4,862,889 | 9/1989 | Feucht . |
| 4,909,069 | 3/1990 | Albin . |
| 4,910,803 | 3/1990 | Cukier . |
| 4,914,395 | 4/1990 | Hamada . |
| 4,942,313 | 7/1990 | Kinzel . |
| 4,956,635 | 9/1990 | Langdon . |
| 4,961,339 | 10/1990 | Kleis . |

FOREIGN PATENT DOCUMENTS

| | | |
|---|---|---|
| 24540371 | 4/1975 | Fed. Rep. of Germany . |
| 2208300 | 6/1974 | France . |
| 0712082 | 1/1980 | U.S.S.R. ............................... 606/34 |

OTHER PUBLICATIONS

"Device to Detect Glove Defects in Development", *Health Industry Today*, Jan. 1990.

"Testing of the Barrier Function of Condoms: An Overview", Schmukler, Robert; Casamento, Jon; Baier, Robert E.; Beard, Richard B.

*Primary Examiner*—Lee S. Cohen
*Attorney, Agent, or Firm*—Pravel, Gambrell, Hewitt, Kimball & Krieger

[57] ABSTRACT

An apparatus and method for detecting adulteration or a condition of near-adulteration of a glove used in critical use application such as in surgery where the gloves are worn by the surgeon and are exposed to the body fluids of a patient. The apparatus and method includes the detection not only of a particular level of conductivity which may be caused by a hole or thin spot in the glove but also the detection of a sudden change in conductivity which may be caused by a sudden change in the condition of the glove, such as the opening of a hole or a sudden thinning of the glove. In this manner, the apparatus and method provides detection not only for an actual condition of the glove but also for a change in condition of the glove. In addition, the circuit is a low impedance circuit, which automatically and continuously discharge static charge build-up on the surgeon.

21 Claims, 2 Drawing Sheets

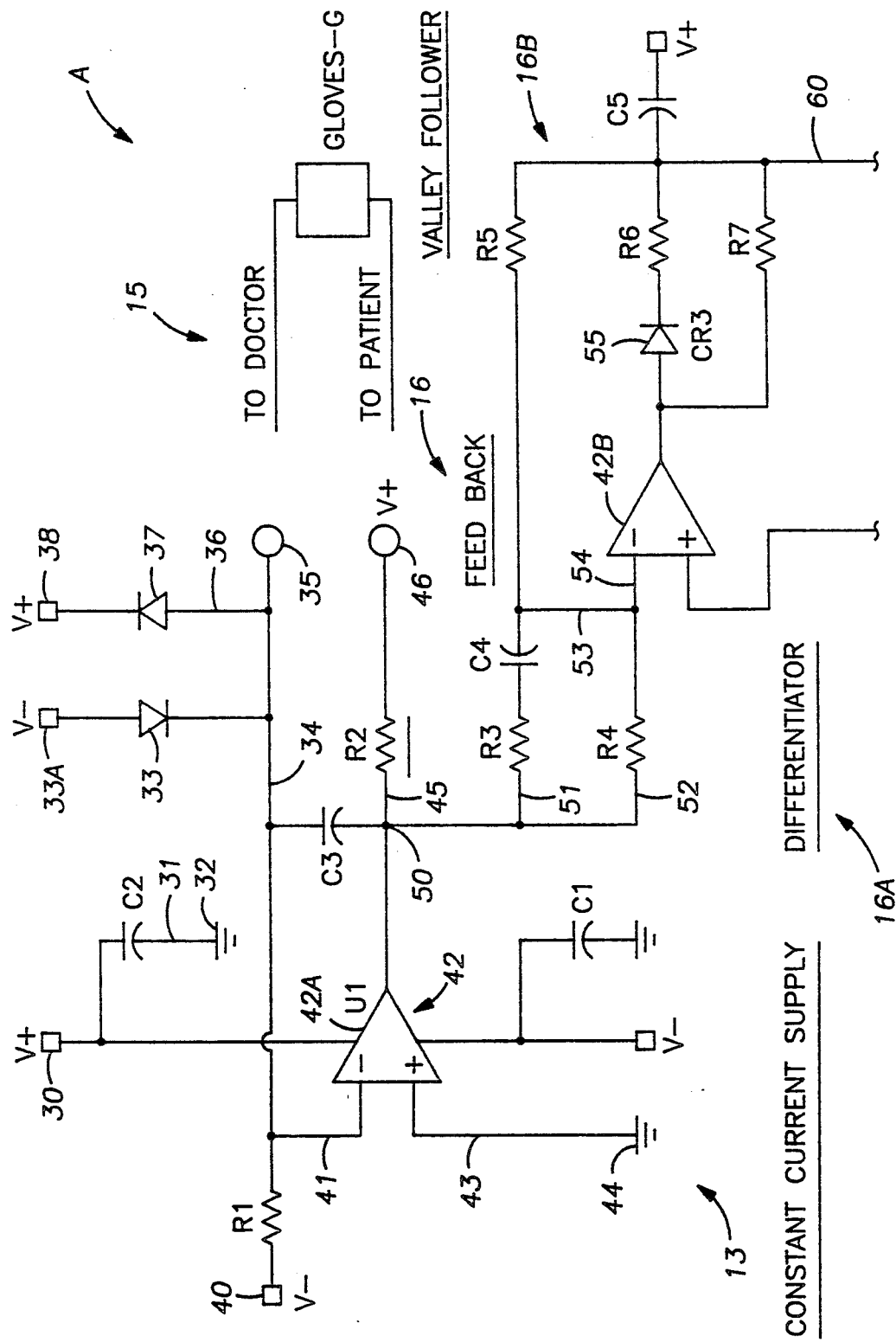

METHOD AND APPARATUS FOR DETECTING ACTUAL OR LIKELY ADULTERATION OF CRITICAL USE GLOVES

FIELD OF THE INVENTION

This invention relates to the detection of actual or likely adulteration of critical use gloves, such as gloves used during surgery, in order to prevent or minimize the adulteration of such gloves with patient body fluids.

BACKGROUND OF THE INVENTION

The adulteration of gloves used in surgery has long been a problem to the medical doctor. Glove adulteration as used herein is intended to encompass glove conditions such as holes formed during manufacture as well as holes formed thereafter for any reason. The term "holes" includes incipient holes, which may be too small to pass water but may enlarge over time, or otherwise breach or deteriorate the integrity of the glove wall. There are two sources for the creation of holes or perforations in surgical gloves. One source is the manufacturer who, due to lack of quality control or inherent manufacturing problems, may manufacture and sell gloves which already have perforations. Recently, the Federal Food and Drug Administration has determined by field inspection failure rates of three to sixteen percent in surgical gloves. The FDA further found that, for patient-examination gloves, average defect rates range from fourteen to eighteen percent. In a recent attempt to tighten the quality control in surgical gloves, the FDA has resorted to the well-known and fundamental technique for determining defects in gloves—a water fill test. The water fill test is only capable of detecting holes large enough to actually pass water. Danger exists when a hole is large enough to expose skin on the other side of the glove to harmful bacteria or virus even though the hole is not large enough to actually allow water to pass through the hole during the water fill test.

The second source of holes or perforations in gloves occurs during use. For example, holes or dangerously thin spots may develop in gloves at the time that the surgeon first fits the gloves over his or her hands, or, a glove may be perforated during surgery. Perforations during surgery can occur because of sharp objects or because of the breaking down of inherently thin spots in the gloves or areas made thin as a result of putting the glove on the hand. Perforations expose the surgeon to actual or possible adulteration of the surgical gloves with body fluids. While such adulteration has always been a possible source of infection or the spreading of bacteria to the surgeon, the alarming spread of the hepatitis and AIDS viruses has created an even more serious problem—the possible spread of an incurable disease to the surgeon. Therefore, the need for accurate and immediate detection of actual or near-adulteration in surgical gloves is now at a heightened level because of the potential for the spread of incurable diseases from patient to surgeon or vice-versa.

The problems with the AIDS virus is not limited, however, to surgeons. For example, it is possible that other users of critical use gloves such as dentists may be subject to many of the same serious concerns because the dentist is also exposed to body fluids during his or her work on a patient. While perhaps less likely, there is also some possibility for the spread of serious diseases from patients to doctors during physical examinations. For purposes of definition, doctors, dentists, nurses and others who may be exposed to disease through gloves or other barriers are defined herein as "health are workers."

While the FDA has taken the approach of using a tried and true method of simple water fill to determine leaks in gloves as manufactured, it is obvious that such simple techniques cannot be used to detect actual or near-adulteration in gloves during use. There have been some attempts in the prior art to detect the occurrence of perforations in surgeons gloves after the gloves are on the doctor's hands. U.S. Pat. No. 4,321,925 of John Hoborn and Ulrich Krebs discloses an electronic detector arranged so that the level of electronic conductivity through the gloves and between the patient and the surgeon may be sensed at regularly recurring discrete time intervals in order to measure a predetermined level of sensed conductivity and signal an alarm if such predetermined level is met.

The detecting circuit of the '925 patent is actually located in one of the shoes of the surgeon and includes one contact located in the insole of the shoe in order to make electrical contact with the surgeon and a second contact exposed to an electrically conducting plate located on the floor of the operating room so that a closed circuit is formed between the operating table, the patient, the doctor, the electronic device located in the shoe and the round conducting element or plate located on the floor of the operating room. The '925 patent teaches that five times per second the disclosed circuit short-circuits the contacts in the insole and in the bottom of the sole of the shoe in order to discharge static electricity from the insole contact which may have accumulated from the doctor. After each short circuit, the circuit is opened between the two contacts and a voltage level sensor is used to detect the electrical conductivity which occurs externally between the contacts.

The impedance of the rubber or latex which comprises the surgical gloves is high. If there is a perforation in the operating gloves of the surgeon, the impedance is thereby reduced and a greater conductivity is provided through the gloves. The '925 patent teaches that the occurrence of a perforation in the operating gloves may allow a relatively high electric conductivity between the surgeon and patient thus allowing the sensing device to sound an alarm upon the occurrence of a predetermined level of sensed conductivity.

Setting of the appropriate level of conductivity is strictly a matter of design and thus it is believed that one drawback to the device of the '925 patent is that the level of conductivity required to trigger the alarm may differ from glove to glove, depending upon the nature of the material, the thickness of the material and any other factors which may impact upon the general conductivity of the series circuit, which includes not only the doctor and patient, but also the doctor's shoes, a round plate located on the operating floor, and the operating table itself. Therefore, the '925 patent may work fairly well for certain types of gloves whose characteristics conform to the particular voltage level chosen for the voltage level sensor, but the '925 patent may not work well with many other types of gloves. In order to function properly, the voltage sensor in the '925 patent may have to be adjusted depending on the type of gloves used. The fact that the absolute conductivity of a glove may vary with the amount of water absorbed in the glove material may also detract from the efficiency of the sensor of the '925 device.

Other prior art devices include several devices which have been disclosed in patents which utilize a basin of conductive fluid in which the surgeon places his or her gloved hands for the purposes of determining whether or not the glove may become adulterated due to immersion. If the conductive fluid in the basin enters a gloved hand, increased conductivity is detected. Other devices and relevant prior art are discussed in an Information Disclosure Statement.

It is submitted that there is need for the development of further, more sophisticated detection methods and apparatus in order to detect not only actual adulteration but near-adulteration of surgical or other critical use gloves. This detection method should also preferably not interfere with the normal activities of the user. The terms "near" or "likely" adulteration of the glove are intended to mean that a hole has just formed or a thin spot had suddenly developed which greatly increases the chances of actual adulteration. In addition, there is a need for detection methods which do not necessarily depend on the absolute level of conductivity of particular operation gloves but are capable of detecting changes in glove condition.

SUMMARY OF THE INVENTION

The present invention comprises method and apparatus for detecting adulteration or a condition of near-adulteration of a glove used in critical use application such as in surgery where the gloves are worn by the surgeon and are exposed to the body fluids of a patient. The invention includes an electronic circuit which includes the basic elements of a power means, first and second leads for electrical attachment to the surgeon and to the patient, feedback detection means and signal alarm means to provide one or more signals in response to a condition of adulteration or near-adulteration of a surgical glove or to a change in glove condition which indicates that the glove has become or is likely to be soon adulterated.

The electronic circuit of this invention has a power means which includes means for providing a supply current to first and second leads such that a series connection is available from the first lead, through the surgeon, the gloves and the patient. Feedback detection means are provided for detecting the actual condition or a change in condition of a glove indicating adulteration and/or near-adulteration and providing feedback signals indicative thereof. A signal alarm means is operably connected to the feedback detection means for providing one or more alarm signals responsive to the feedback signals such that conditions of adulteration and/or near-adulteration of a glove are detected. The apparatus and method of this invention includes the detection not only of a particular level of conductivity which may be caused by a hole or thin spot in the glove but also the detection of a sudden change in conductivity which may be caused by a sudden change in the condition of the glove, such as the opening of a hole or a sudden thinning of the glove. In this manner, the invention described here provides detection not only for an actual condition of the glove but also for a change in condition of the glove. In addition, the circuit is a low impedance circuit, which obviates the necessity of periodic static electrical discharge in the circuit such as required by the invention of the '925 patent.

This description of the invention is intended as a summary only. The actual scope of the invention sought to be protected is set forth in the claims and the preferred embodiment for the invention is hereinafter described. It is not intended for any of the statements in this Summary of the Invention to be a limitation upon the actual or ultimate scope of the patent coverage obtained.

BRIEF DESCRIPTION OF THE DRAWINGS

A better understanding of the present invention can be obtained when the following detailed description of the preferred embodiment is considered in conjunction with the following drawings, in which:

FIGS. 1A and 1B disclose the electronic circuitry in schematic form for the apparatus and method of this invention.

DESCRIPTION OF THE PREFERRED EMBODIMENT

Figure 1B:
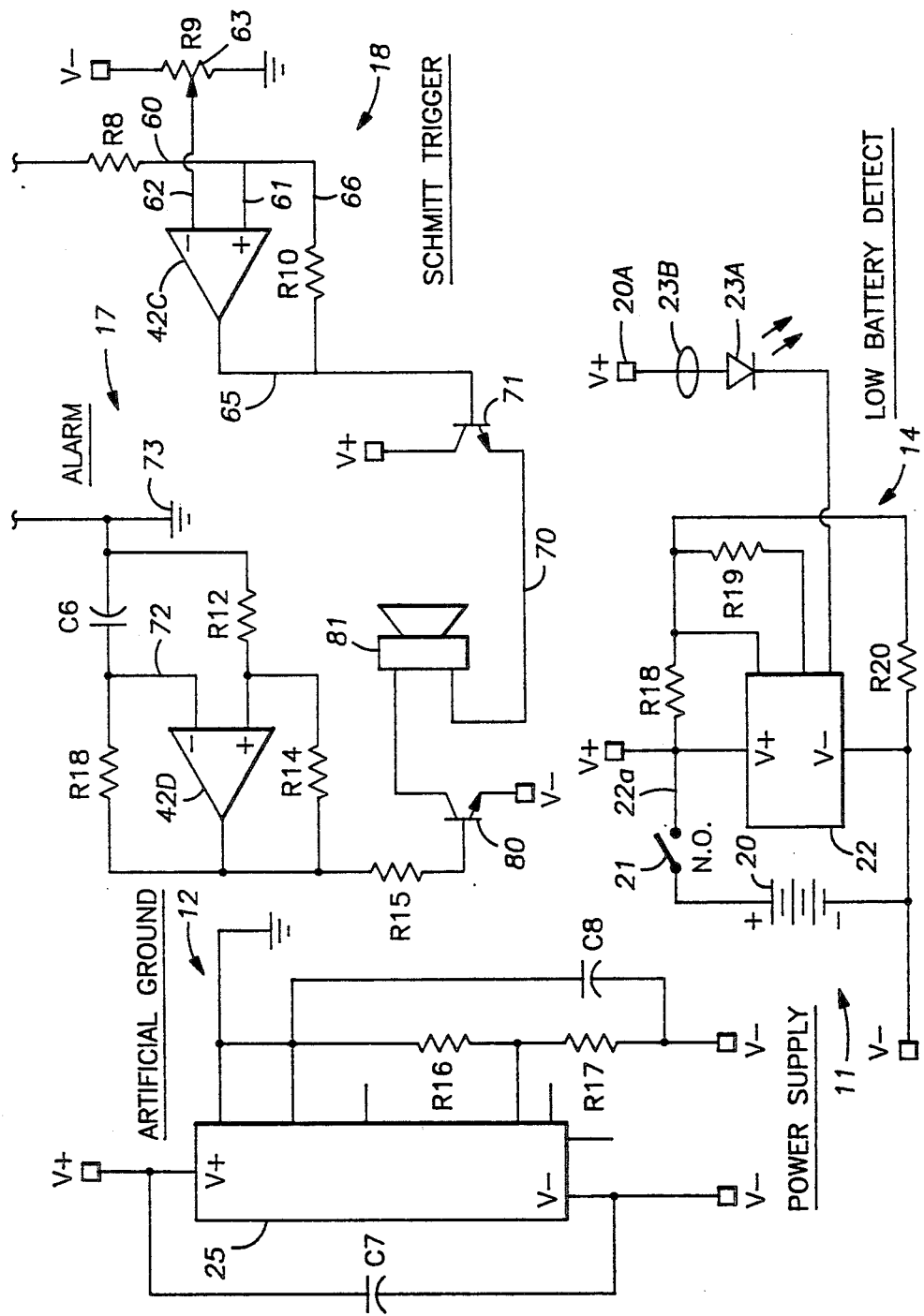

Referring to the drawings, the schematics illustrated in FIGS. 1A and 1B combine to provide the method and apparatus of this invention generally designated as A for detecting adulteration or a condition of near-adulteration of a critical use glove. The term "critical use" applies to gloves used by persons such as surgeons, dentists, nurses or other health care workers who may be exposed to serious and perhaps incurable diseases or other dangers as a result of glove deterioration. While the environment for use will be described here as during surgery, it should be understood that the term "surgery" includes any critical use such as emergency room, labor and delivery, intensive care, that is, whenever a gloved hand may be exposed to body fluids of another or to any other potentially harmful fluid. The apparatus A of this invention is actually illustrated in two parts, one part of the circuit being illustrated in FIG. 1A and the other part of the circuit being illustrated in FIG. 1B; thus, the figures in combination show the complete apparatus of the present invention.

Basically, the apparatus A includes a power supply section 11, an artificial ground generation section 12 which generates an artificial ground throughout the circuit, and a section 13 which provides a constant current supply. A low battery detect circuit 14 is also provided in conjunction with the power supply section 11 in order to provide an alarm when the battery drops below a certain voltage level. The constant current supply circuit 13 provides a constant source of current, without interruption, to a series circuit generally designated as 15 which includes the doctor, the surgical gloves G worn by the doctor and the patient. A Feedback Circuit generally designated as 16 includes a Differentiator circuit 16A, a circuit referred to as a Valley Follower circuit 16B and Schmitt trigger 18 for detecting actual or near-adulteration of a glove G. "Valley Follower" is a term used herein to describe a circuit similar to a more commonly known circuit known as a Peak Follower, except that a Valley Follower follows the valley or lowest peak rather than the highest peak. In response to the actual state or condition of the glove and/or to the change in state or condition of the glove, which indicates adulteration or near adulteration, an alarm circuit generally designated as 17 is provided to sound an audible alarm or provide other alarm signal, visible or audible.

The power supply section 11 is comprised of a nine-volt battery 20. The nine-volt battery 20 provides a split voltage having a positive voltage potential referred to as v+ and a negative voltage potential referred to as v−. The split voltages v+ and v− are provided as voltage supplies throughout the circuit, as shown. Positive voltage potential is indicated by v+ at various voltage input points throughout the circuitry. Similarly, the negative voltage potential is designated as v− and connections to negative voltage levels provided by the split voltage of circuit 11 are indicated throughout by v−.

The split voltages v+ and v− are provided to the artificial ground circuitry 12 in order to generate an artificial ground for the circuit as shown. The split voltage circuit 12, as illustrated in FIG. 1B, is comprised of a standard micropowered voltage regulator generally designated as 25 which is connected through v+ and v− connector points to the power supply circuit 11 and, through voltage regulator 25, acts to generate an artificial ground designated as "gnd" that is at a voltage level midway between the split voltages v+ and v−. The voltage regulator includes biasing resistors R16 and R17, which in conjunction with capacitor C8, act to provide the artificial ground gnd, as is well known to those skilled in the art. The artificial ground connections are indicated by the "gnd" designation at various points throughout the circuitry. The artificial ground connections act as a stabilizing factor in the circuit.

The battery 20 is also included in a low battery detection circuit generally designated as 14 which includes a manually operated on/off switch 21 which connects the battery through line 22a to a voltage level detector 22. The voltage level detector 22, in conjunction with resistors R18, R19 and R20 is designed to detect a reduction in voltage below, for example, 7.5 volts if a nine-volt battery is utilized. The low battery detector circuit 14 is connected through diode 23A to a light emitting diode 23B to provide a visible signal.

The constant current supply generally designated as 13 is provided by the op amp section 42A (to be hereinafter described) which provides a constant current source through line 45 to connector 46, glove G, connector 35 and return line 34. Current line 34 terminates in a suitable connector 35 which is designed to be attached to a doctor in order to receive the very low constant current, preferably in the submicro amp range, from line 45 through the patient, the gloves G 15 and the doctor. The capacitor C2 connected through line 31 to the positive voltage source 30 is to provide stability to the op amp 42 as recommended by the manufacturer. Should for any reason the voltage potential of the doctor exceed the positive reference voltage v+, line 36 branching from constant current line 34 includes diode 37 in series connection to a positive voltage reference v+ at 38 in order to allow for the conduction of any current outwardly away from the doctor in the event of such condition. Similarly, should a negative voltage potential of the doctor through lead 35 exceed a predetermined level, the diode 33 in line 31a branching from constant current line 34 will provide for the conduction of any excess current directly to negative supply 33a. The electrical connector 35 may be a standard type of electrical connector used in the operating room, such as an EKG patch or some type of quick disconnect so that the circuit can be quickly removed from the doctor.

The reference voltage v− at 40 in line 34 is set through resistor R1, which is connected through line 41 to an operational amplifier or "op amp" generally designated as 42. The op amp used in the present invention are preferably TLC 1079C op amps (available from Texas Instruments) or other comparable op amps which include MOSFET Metal Oxide Semiconductor Field Effect Transistors inputs to account for the high impedance inputs. The op amp 42 is a quad op amp, meaning four sections 42A–42D are available for amplifier functions in the circuit. The op amp 42 is preferably a micropowered operational amplifier capable of swinging to, and common mode input voltage including, a negative supply voltage. Other op amps or individual transistorized circuitry elements may be used to provide similar operating characteristics. The op amp section 42A, as illustrated, is referenced to both positive and negative battery potentials, and is set at the bias for conduction of the op amp section 42A through line 41 connected to line 34 and to the negative voltage potential through resistor R1. The noninverting terminal of the op amp section 42A is connected to line 43 to ground at 44. The op amp section 42A includes output line 45 which includes resistor R2 in series with its termination connector 46 which is adapted to be connected to the patient to provide the constant submicroamperage current in series to connector 46, the patient, glove G, the doctor and line 34 to the negative voltage 40 through resistor R1.

The connector 46 may be of the same type as described with respect to connector 35 and thus may be of a quick disconnect or other suitable variety. Similar to capacitor C2, capacitor C1 is connected to ground "gnd" to provide for purpose of adding stability to the op amp 42. Capacitor C3 connected between lines 34 and 45 act as a filter to filter external noise originating from other devices in the operating theater and to stabilize the operation of the power supply.

It is anticipated that the entire apparatus A will be packaged in a cartridge-like housing and carried by the doctor and thus the actual constant current supply line or lead 34 leading to connector 35 will be relatively short since it will be extending only from the apparatus A into connection with the skin of the doctor while the lead line 45 will extend from the unit into electrical connection with the patient through connector 46 and thus will be a longer lead line. The gloves G as illustrated provide the only source of conductivity between the doctor and patient and thus detection of conditions or change in conditions across the gloves G may be detected. Conversely, the unit may be placed on the table with the patient receiving lead 34 and connector 35 and the doctor receiving the long lead and connector 46. Also, the term "doctor" includes any glove wearer at risk including nurses, undertakers and others, all of whom are within the definition "health care workers."

The purpose of the negative potential connection 40 to resistor R1 in conjunction with op amp section 42A, is to maintain power supply line 34 at a virtual ground. In this manner and as described earlier, any undesirable increase in voltage potential at the lead 35 attached to the doctor causes conduction through diode 33 to ground 32. This occurs without the need for periodic interruption of the constant current supply, thus automatically and continuously discharging static charge build-up on the surgeon.

In summary, the op amp section 42A converts the negative voltage reference into a submicroamp signal such as in the range of 600 Nano amps (approximate) in order to provide a constant current maintained through the op amp section acting as a voltage to current converter so that a constant current is supplied through series connection to lines 45, lead 46, glove G and line 34 through R1 to negative voltage 40. The capacitor C3 connected between line 45 and 34 is provided to act as a filter to filter external noise originating from other devices in the operating theater. The actual hookup to the patient includes the current limiting resistor R2 to assure that in the worst case, the current remains below 10 micro amps and is therefore intrinsically safe. Lead 34 is connected to the inverting input of the op amp section 42A through line 41 in order to maintain a current-to-voltage conversion at a virtual ground potential. The development of a virtual ground potential in conjunction with the two low leakage clamping diodes 33 and 37, serve to protect the doctor even in cases where he may neglect to disconnect from the patient during use of other electrical equipment such as during defibrillation.

The output of the constant current stage is a voltage at node 50 which is proportional at any point in time to the overall resistance of the doctor-patient system including the glove G. The Feedback circuit 16 is designed to detect the voltage level and changes in the voltage level at node 50. The detected voltage at 50 passes as a signal through the Differentiator circuit 16a, which includes lines 51 and 52 which are interconnected by line 53 to provide input through line 54 to one terminal of a second section 42B of op amp 42. The combination of resistors R3 and R4 in conjunction with capacitor C4 provides a differentiated signal through line 54 to the op amp section 42B. The purpose of differentiating the signal from node 50 is to provide a signal responsive to the rate of change of the voltage at line 50, which is responsive to a rate of change in condition of a glove G. In addition to providing a signal responsive to the rate of change at feedback node 50, the level of voltage feedback node 50 is also detected through resistor R4 for detecting the absolute voltage at node 50 at any point in time.

To detect rapid decreases in resistance possible when a glove is punctured or subject to other sudden deterioration, such as for example a sudden thinning, the circuit includes a stage referred to as a Valley Follower circuit 16B. The Valley Follower circuit 16B includes the op amp section 42B that uses resistor R5 to set the overall gain at unity for level sensing and at some ratio such as 10 to 1 for detecting rapid rates of change in the voltage at node 50. The op amp section 42B is designed in combination with the Differentiator circuit 16 to amplify slow changing voltage feedback signals at 50 at near unity and to amplify differentiated, quickly declining voltages at about ten to one and invert such signals. The Valley Follower circuit 16B is essentially an inverted peak follower and acts to sample and hold the lowest amplified and inverted signal from the Differentiator 16A. The op amp section 42B comprises an inverting stage such that the output becomes more positive as the glove's conductivity degrades. Therefore, the greater negative change in voltage at feedback node 50 will, through op amp section 42B, provide the most positive value. This is accomplished through a combination of diode 55 and resistor R6 added to current limit the op amp output. The Valley Follower circuit 16B is further designed to drain off anomalous spikes, such as due to interference from other equipment, physical factors, etc., via resistor R7, which assures that an anomalous spike will sound the alarm for a predesignated maximum number of seconds. The purpose of the Valley Follower circuit 16B is to measure the latest reductions in conductivity across the glove G by measuring the latest reduction in voltage at feedback node 50 and to react to the latest reduction, which is amplified and inverted, and provide a signal in response to reductions in voltage at feedback node 50 of a predetermined value (due to inversion of the signals through the op amp section 42B).

The Schmitt trigger circuit 18 receives analog signals from the Valley Follower circuit indicating a predesignated level of conductivity within the glove G or a rapid change in conductivity within the glove G, as detected at feedback node 50. The Schmitt trigger detects and passes forward those analog signals of a certain positive increasing magnitude from the Valley Follower through line 60. Line 60 is connected through line 61 to one input of an op amp section 42C, while the other input to the op amp section 42C is connected through line 62 to a variable voltage potential 63, which may be a level setting potentiometer which may be operated by a dial or other means. The output of the op amp section 42C is provided through line 65 with the hysteresis being set by resistor R10 in line 66. The output of the op amp section 42C is provided to an NPN transistor 71, which is designed to trigger Alarm circuit 17.

The Alarm circuit 17 includes an op amp section 42D, which acts as an oscillator. The op amp section 42D in combination with resistor R18A and capacitor C6 provides an oscillating signal to transistor 80. A signal through op amp 42C in line 65, which is in response to a hole in the glove, biases the base voltage of the transistor 71 causing conduction of the transistor 71, collector to emitter, which transmits a signal through line 70 to alarm 81. The oscillated output to transistor 80 by op amp section 42D drives transistor 80 to allow conduction of transistor 80, collector to emitter to ground, such that current flows through speaker alarm 81. The alarm 81 sounds whenever the oscillating signal through transistor 80 is allowed to conduct through the alarm, which occurs when the Schmitt trigger 18 transistor 71 conducts through line 70. The alarm 81 may be a piezo electric speaker 81, or any other suitable alarm.

Thus, in the apparatus A as well as in the method practiced and taught by this invention 50, a submicroamperage current is supplied at a constant low level, without interruption, to the doctor and patient with the glove G being the potentially conductive point of connection between the doctor and patient. A voltage feedback from the doctor-glove-patient circuit is monitored at all times and the actual feedback voltage and the rate of changes in feedback voltage are detected. The rate of change of feedback voltage is amplified and both signals, feedback voltage level and the amplified rate of change in feedback voltage are provided as feedback signals. Whenever the signal or signals are within the predignated parameter for alarm, the signal or signals are squared and transmitted to alarm circuitry for visible and/or audio announcing.

In this manner, this invention operates to detect the rate of change of conductivity across the glove, which is a feature which is highly advantageous because the rate of change of conductivity across the glove may be detected regardless of the level of conductivity in the glove at any one time. Therefore, even though particular gloves in new condition, without perforations or thin spots or other deterioration, may have differing levels of conductivity, the ability to measure the relative rise in conductivity of a particular glove with respect to time allows for the detection of the sudden development of a hole or development of a sudden thin spot. Therefore, the method and apparatus of this invention as practiced provides method and apparatus for detecting two different conditions of a particular glove, the actual conductivity across the glove at any one time or a change in conductivity with respect to time across the glove. Detection of the level of conductivity at any particular time allows the method and apparatus of this invention to detect the presence of a hole or the development of a hole or other deterioration during use. Of course, the ability to detect deterioration allows this invention to detect not only actual adulteration but also near adulteration. The ability to detect actual and/or near-adulteration of the glove is highly refined by the ability to detect changes in conditions of conductivity over time. Thus, if a glove develops a hole suddenly, the rate of change of conductivity is measured, detected and an alarm sounded. If a glove develops a sudden thin spot, that rate of change of conductivity is also detected and thus a condition of near adulteration or likely adulteration may also be detected. Further, the apparatus and method of this invention provides means for dissipation of any static electricity or other voltage potential buildup in the doctor without having to interrupt the constantly supplied submicroamberage current supply of the apparatus to the doctor. This is provided by setting the constant current input at a virtual ground level so that any voltage potential above ground may be drained off through the circuitry without the need for any periodic interruption of the constantly supplied current. This feature of the invention is actually an additional or backup safety feature since the invention includes the development of a power supply in the submicroamperage range which will act to minimize the development of static electricity buildup any way.

The foregoing disclosure and description of the invention are illustrative and explanatory thereof, and various changes in the size, shape, materials, components, circuit elements, wiring connections and contacts, as well as in the details of the illustrated circuitry and construction may be made without departing from the spirit of the invention. For example, while this invention has been described as particularly applied to critical use gloves, it is intended that this invention applies to any other barrier-type relatively thin-membraned material such as condoms. While the circuitry disclosed here is integrated or combinatorial, it should be understood that equivalent circuitry may be provided by digital hardware and software. While the power supply is described as direct current, an alternating current power supply may be utilized and suitable circuitry provided to convert the feedback signal to direct current to detect changes in condition of the glove. This invention has been described in terms of detecting danger to the glove-wearer. The same concepts prevent the danger of spread of disease or infection from the gloved hand to the patient.

We claim:

1. Apparatus for detecting adulteration or a condition of near-adulteration of a glove used in critical use applications such as in surgery where gloves are worn by a health care worker and are exposed to the body fluids of a patient, comprising:

an electronic circuit including power means, first and second leads for electrical attachment to the health care worker and to the patient, feedback detection means and signal alarm means to provide one or more signals in response to a condition of adulteration or near-adulteration of a surgical glove;

said power means includes means for providing a supply current to said first and second leads such that a series connection is available from said first lead, through said health care worker, said gloves and said patient depending upon the condition of said gloves;

said feedback detection means for detecting adulteration and/or near-adulteration of a glove through detection of the condition and rate of change in the electrical condition of a glove and providing feedback signals indicative thereof; and said signal alarm means operably connected to said feedback detection means for providing one or more alarm signals responsive to said feedback signals such that condition of adulteration and/or near-adulteration of a glove is detected.

2. The structure of claim 1, comprising:

said power means includes a constant current source for providing a constant current to said series connection of said first and second leads, said health care worker, said gloves and said patient.

3. The structure of claim 1, comprising:

said feedback detection means includes means for providing a first feedback signal in response to a predesignated conductivity which indicates the presence of an actual failure point or point of likely failure of one of said gloves.

4. The structure of claim 1, comprising:

said feedback detection means includes means for providing a feedback signal responsive to a predesignated rate of change of conductivity which indicates the sudden creation of a hole or other deterioration of the glove.

5. The structure as set forth in claim 4 wherein the feedback means, further includes:

differentiator means for differentiating a signal from said series connection in order to determine the rate of change of condition in said series connection in response to rapid deterioration of one of said gloves such as in response to a sudden tear, puncture or other actual or likely failure of one of said gloves.

6. The structure as set forth in claim 1, comprising:

said power means providing means to ground said health care worker in order to prevent any accidental power surge into the health care worker with periodic interruption of said power means.

7. The structure as set forth in claim 1 wherein said feedback detection includes:

means for discerning between slow changing feedback signals and quickly declining feedback signals and amplifying said quickly declining feedback signals to said signal alarm means.

8. Apparatus for detecting adulteration or a condition of near-adulteration of a glove used in critical use applications such as in surgery where gloves are worn by a health care worker and are exposed to the body fluids of a patient, comprising:

an electronic circuit including power means, first and second leads for electrical attachment to the health care worker and to the patient, feedback detection means and signal alarm means to provide one or more signals in response to a condition of adulteration or near-adulteration of a surgical glove;

said power means includes means for providing a supply current to said first and second leads such that a series connection is available from said first lead, through said health care worker, said gloves and said patient depending upon the condition of said gloves;

said feedback detection means includes means for detecting adulteration and/or near-adulteration of the glove through detection of the rate of change of conductivity across the glove and providing feedback signals indicative thereof; and said signal alarm means operatively connected to said feedback detection means for providing one or more alarm signals responsive to said feedback signals such that conditions of adulteration and/or near-adulteration of the glove are detected.

9. The structure as set forth in claim 8, including:

said feedback detection means includes means for providing a feedback signal responsive to a predesignated rate of change in conductivity which indicates the sudden creation of a hole or other deterioration of the glove.

10. The structure as set forth in claim 9 wherein the feedback means further includes:

differentiating means for differentiating a signal from said series connection in order to determine the rate of change of condition in said series connection in response to deterioration of one of said gloves with respect to time such as in response to a sudden tear, puncture or other actual or likely failure of one of said gloves.

11. The structure as set forth in claim 8, further including:

said power means including means for providing a constant supply current to said first and second leads wherein such constant supply current is at a low microamperage level to avoid any possible harm to health care worker or patient.

12. The structure as set forth in claim 8, including:

said power means includes means for connecting the health care worker to an artificial ground in the circuit to continuously and automatically minimize the buildup of static electricity potential within the health care worker and thus avoid the need for interruption of the supplied current.

13. The structure as set forth in claim 8 wherein said feedback detection includes:

means for discerning between slow changing feedback signals and quickly declining feedback signals and amplifying said quickly declining feedback signals to said signal alarm means.

14. A method for detecting adulteration or a condition of near-adulteration of a glove used in critical use applications such as in surgery where gloves are worn by a health care worker and are exposed to body fluids of a patient, comprising the steps of:

providing a constant power supply of low microamperage current through a first lead attached to a health care worker and a second lead attached to patient such that the actual low microamperage current passing health care worker to patient is dependent upon the conductivity across the gloves worn by the health care worker;

detecting a predesignated rate of change of conductivity across the gloves; and providing an alarm signal in response to said predesignated rate of change of conductivity across a glove worn by the health care worker in order to provide one or more alarm signals responsive to the rate of change of conductivity such that a condition of adulteration and/or near adulteration of a glove is detected.

15. The method of claim 14, further including the step of:

detecting the rate of change of conductivity across said glove by differentiating with respect to time any current passing through said glove and providing an alarm signal in response to a predetermined rate of change of condition of said glove.

16. Apparatus for detecting adulteration or a condition of near-adulteration of a barrier used in critical use applications where disease may be transmitted between first and second persons, where the barrier is positioned between the first and second persons comprising:

an electronic circuit including power means, first and second leads for electrical attachment to the first and second persons, feedback detection means and signal alarm means to provide one or more signals in response to a condition of adulteration or a near-adulteration of a surgical barrier;

said power means including means for providing a supply current to said first and second leads such that a series connection is available from said first lead, through said first person, said barrier and said second person depending upon the condition of the barrier;

said feedback detection means detecting adulteration and/or near-adulteration of said barrier through detection of rate of change of the electrical properties of the barrier and providing feedback signals indicative thereof; and said signal alarm means operably connected to said feedback detection means for providing one or more alarm signals responsive to said feedback signals such that a condition of adulteration and/or near-adulteration of said barrier is detected.

17. The structure as set forth in claim 16, comprising:

said power means including a continuous current source for providing a continuous current to said series connection of said first and second leads, said first person, said barrier and said second person.

18. The structure as set forth in claim 16, including:

said feedback detection means includes means for providing a first feedback signal in response to a predesignated conductivity which indicates the presence of an actual failure point or a point of likely failure of said barrier.

19. The structure as set forth in claim 16, further said feedback detection means includes means for providing a feedback signal responsive to a predesignated rate of change of conductivity which indicates the sudden creation of a hole or other deterioration of said barrier.

20. The structure as set forth in claim 18, including:

said feedback detection means further includes means for providing a second feedback signal responsive to a predetermined rate of change in conductivity which indicates the sudden creation of a hole or other deterioration of said barrier.

21. The structure as set forth in claim 19, said feedback detection means further including:

differentiator means for differentiating a signal from said series circuit in order to determine the rate of change of condition of said circuit in response to rapid deterioration of a barrier such as in response to a tear, puncture or other actual or likely failure of said barrier.

* * * * *